United States Patent
Jadhav et al.

(10) Patent No.: US 11,938,110 B2
(45) Date of Patent: Mar. 26, 2024

(54) USE OF VERAPAMIL FOR THE TREATMENT OF SARS-COV-2 INDUCED COVID-19

(71) Applicant: Manoj P. Jadhav, Hillsborough, NJ (US)

(72) Inventors: Manoj P. Jadhav, Hillsborough, NJ (US); Ramakrishna Devarakonda, Richmond, TX (US)

(*) Notice: Subject to any disclaimer, the term of this patent is extended or adjusted under 35 U.S.C. 154(b) by 0 days.

(21) Appl. No.: 18/304,306

(22) Filed: Apr. 20, 2023

(65) Prior Publication Data

US 2023/0255924 A1    Aug. 17, 2023

Related U.S. Application Data

(63) Continuation of application No. 17/234,112, filed on Apr. 19, 2021.

(60) Provisional application No. 63/016,595, filed on Apr. 28, 2020.

(51) Int. Cl.
| | | |
|---|---|---|
| A61K 31/277 | (2006.01) | |
| A61K 9/00 | (2006.01) | |
| A61K 47/02 | (2006.01) | |
| A61P 31/14 | (2006.01) | |

(52) U.S. Cl.
CPC .......... *A61K 31/277* (2013.01); *A61K 9/0078* (2013.01); *A61K 47/02* (2013.01); *A61P 31/14* (2018.01)

(58) Field of Classification Search
CPC ............................ A61K 31/277; A61P 31/14
See application file for complete search history.

(56) References Cited

U.S. PATENT DOCUMENTS

| | | | |
|---|---|---|---|
| 6,190,691 B1 * | 2/2001 | Mak ..................... | A61K 31/554 604/20 |
| 2004/0068222 A1 * | 4/2004 | Brian ................... | A61M 11/002 604/152 |
| 2004/0167117 A1 | 8/2004 | Adams | |
| 2005/0191245 A1 | 9/2005 | Adams | |
| 2005/0245502 A1 | 11/2005 | Keller | |
| 2008/0038363 A1 * | 2/2008 | Zaffaroni ............. | A61M 11/041 424/502 |

FOREIGN PATENT DOCUMENTS

| | | | | |
|---|---|---|---|---|
| WO | WO-2021181279 A1 * | 9/2021 | ........... | A61K 31/231 |
| WO | WO-2021183463 A1 * | 9/2021 | ........... | A61K 39/215 |

OTHER PUBLICATIONS

Si et al., "Human organs-on-chips as tools for repurposing approved drugs as potential influenza and COVID19 therapeutics in viral pandemics", bioRxiv preprint doi: https://doi.org/10.1101/2020.04.13.039917. Apr. 15, 2020. (Year: 2020).*

"Nifedipine and Amlodipine Are Associated With Improved Mortality and Decreased Risk for Intubation and Mechanical Ventilation in Elderly Patients Hospitalized for COVID-19," Cureus, May 12, 2020, DOI: 10.7759/cureus.8069.

Author Correction: Calcium channel blocker amlodipine besylate therapy is associated with reduced case fatality rate of COVID-19 patients with hypertension. Cell Discov. May 3, 2021;7(1):29.

Calcium channel blocker amlodipine besylate therapy is associated with reduced case fatality rate of COVID-19 patients with hypertension. Cell Discov. Dec. 22, 2020;6(1):96. doi: 10.1038/s41421-020-00235-0. Erratum in: Cell Discov. May 3, 2021;7(1):29.

"The SARS Coronavirus 3a protein binds calcium in its cytoplasmic domain." Virus Res. Oct. 13, 2014;191:180-3. doi: 10.1016/j.virusres.2014.08.001. Epub Aug. 10, 2014. PMID: 25116391; PMCID: PMC7114474.

"SARS-CoV-2, Hypoxia, and Calcium Signaling: The Consequences and Therapeutic Options," ACS Pharmacol. Transl. Sci. 2021, 4, 1, 400-402 https://doi.org/10.1021/acsptsci.0c00219.

"Association of Antihypertensive Agents with the Risk of In-Hospital Death in Patients with Covid-19." Cardiovasc Drugs Ther 36, 483-488 (2022). Https://doi.org/10.1007/s10557-021-07155-5. Posted Nov. 24, 2020.

Non-Final Office Action dated Jan. 11, 2013 in U.S. Appl. No. 17/234,112.

Yazan et al., "Pharmacodynamic Comparison of a Nasal Formulation of Verapamil and Intravenous and Oral Dosage Forms." Drug Development and Industrial Pharmacy, 22(3), 281-284, (1996).

Final Office Action dated May 22, 2023 in U.S. Appl. No. 17/234,112.

Gupta, "Quantitation and stability of verapamil hydrochloride using high-performance liquid chromatography", 1985, Drug Development and Industrial Pharmacy, 11(8), pp. 1497-1506. (Year: 1985).

* cited by examiner

*Primary Examiner* — Michael B. Pallay
(74) *Attorney, Agent, or Firm* — Len Smith; Denise Brown; Transformative Legal LLC

(57) ABSTRACT

The invention relates to methods for treating or preventing infections with coronavirus, in aspects including Severe Acute Respiratory Syndrome Coronavirus 2 (SARS-CoV-2), and SARS-CoV-2-induced COVID-19. The methods comprise administering a pharmaceutically acceptable composition comprising an effective amount of verapamil. In aspects, the composition is administered through pulmonary delivery. In aspects, the composition is administered through a nasal spray. Such methods modulate the entry and replication of coronavirus in host cells and effectively treat coronavirus infection.

2 Claims, 4 Drawing Sheets

| Sl No | Ingredient | Concentration |
|---|---|---|
| 1 | Verapamil hydrochloride | 20 mg/mL |
| 2 | Sodium chloride | 6.25 mg/mL |
| 3 | Distilled water | q.s. to 1 mL |

FIG. 1

| Formulation | 0 time | | 6 days | | 14 days | | 24 days | | 33 days | |
|---|---|---|---|---|---|---|---|---|---|---|
| | Conc. mg/mL (pH) | % peak area | Conc. mg/mL (pH) | % peak area | Conc. mg/mL (pH) | % peak area | Conc. mg/mL (pH) | % peak area | Conc. mg/mL (pH) | % peak area |
| Hanura-1 | 19.9 (5.13) | 99.92 | 19.8 (5.41) | 99.91 | 19.5 (5.38) | 99.89 | 19.5 (5.39) | 99.89 | 19.0 (5.36) | 99.76 |
| Hanura-2 | 19.9 (6.09) | 99.85 | 19.5 (6.07) | 99.91 | 19.5 (6.10) | 99.91 | 19.3 (6.05) | 99.91 | 19.2 (6.15) | 99.80 |
| Hanura-3 | 19.8 (4.63) | 99.87 | 19.7 (4.95) | 99.86 | 19.7 (4.88) | 99.86 | 19.4 (5.09) | 99.87 | 19.1 (4.99) | 99.79 |
| Hanura-4 | 19.2 (5.61) | 99.88 | 19.8 (5.59) | 99.89 | 19.8 (5.62) | 99.91 | 19.6 (5.69) | 99.91 | 19.1 (5.56) | 99.81 |
| Hanura-5 | 20.0 (4.09) | 99.86 | 19.8 (4.27) | 99.87 | 19.8 (4.33) | 99.87 | 19.8 (4.45) | 99.88 | 19.5 (4.39) | 99.82 |

FIG. 2

USE OF VERAPAMIL FOR THE TREATMENT OF SARS-COV-2 INDUCED COVID-19

CROSS-REFERENCE TO RELATED APPLICATIONS

This application is a continuation application of U.S. patent application Ser. No. 17/234,112, filed on Apr. 19, 2021, which claims the benefit of U.S. Provisional Application No. 63/016,595 filed Apr. 28, 2020, all of which are incorporated herein by reference in its entirety.

DESCRIPTION OF THE INVENTION

Technical Field of the Invention

The present invention relates to a formulation of a Calcium Channel Blocker (CCB) through pulmonary delivery using an inhaler, a nebulizer or any other similar delivery system against Severe Acute Respiratory Syndrome Coronavirus 2 (SARS-CoV-2) induced Coronavirus Disease 2019 (COVID-19), SARS, Middle East Respiratory Syndrome (MERS), Influenza and any other respiratory viruses thereof. More particularly, the invention relates to the formulation of calcium channel blockers preferably verapamil hydrochloride through pulmonary delivery as nasal spray for the treatment against COVID-19.

BACKGROUND OF THE INVENTION

COVID-19 is a highly pathogenic respiratory disease, which exhibited an outbreak after its first appearance in Wuhan. China in December 2019. COVID-19 is caused by a novel coronavirus namely SARS-CoV, which causes respiratory illness with elevated fatality rate in patients with one or more of comorbidities such as obesity, hypertension and diabetes.

SARS-CoV-2 causes respiratory illness and breathing complications with symptoms such as fever, cough, dyspnea etc. resulting in multiple organ syndrome and sometimes even death in severe cases similar to SARS-CoV. SARS-CoV-2 infection is observed as a continuation to the global spread of two previously unknown coronaviruses. The first known case of severe acute respiratory syndrome (SARS) was in November 2002 in China. This was followed by Middle East respiratory syndrome coronavirus (MERS-CoV) observed in April 2012.

SARS-CoV-2 is a positive single stranded Ribonucleic acid (RNA) virus with a genome length of approximately 30 kb. SARS-CoV-2 infection is associated with human-to-human transmission, which is the reason for a rapid spread of the infection globally within a short period of time. The World Health Organization (WHO) declared COVID-19 as a pandemic on Mar. 11, 2020. The report states that 2.463.357 confirmed cases of SARS-CoV-2 across 185 countries till date and 169,502 deaths have been reported and still counting. There are 41,575 deaths and over 778,000 positive cases reported in US alone.

SARS-CoV-2 is not capable of replication by self and needs a host cell to replicate and multiply. SARS-CoV-2 exploits the environmental host cell for replication thus inducing host cell dysfunction. SARS-CoV-2-host interaction is the foundation for pathogenesis and associated with disease severity. The modulations of the intracellular environment have become an important strategy in antiviral drug discovery and development.

SARS-CoV-2-host interaction results in the disruption of various cell functions affecting multiple cell processes. One of the processes disrupted by SARS-CoV-2-host interaction is calcium signaling. Calcium is essential for virus entry, viral gene replication, virion maturation and then its release from one cell to the other surrounding cells. The virus disturbs the host cell's calcium homeostasis as one of the strategies to modulate the host cell signaling in the favor of virus. Literally, the viruses hijack the host calcium channels and pumps leading to calcium imbalance in the host cells.

Calcium as an important second messenger, mediates the sensor input and responses output for a majority of cellular processes such as stress responses, synaptic plasticity, immunodefenses, protein transport and endosome formation in mammals. It has been demonstrated that the host cell dysfunction following viral infection is accompanied by abnormal intracellular calcium concentration. SARS-CoV-2 and other like-viruses require intracellular system to achieve successful replication through multiple routes for example, viral proteins directly bind to calcium or disturb the membrane permeability for calcium by manipulating calcium apparatus.

The host cell plasma membrane is the immediate target for the virus to enter the host cell. The plasma membrane comprises multiple channels and pumps that allow the entry of the virus into the host cell. Hence, targeting these calcium pumps or calcium channels such as voltage-gated calcium channels, store-operated channels, receptor operated channels, transient receptor potential ion channels and Calcium ATPase can be one of the targets to prevent the infection in host cells.

It is also observed that intracellular calcium and phospholipase signaling plays an important role in the pathogenesis of Mouse Hepatitis Virus (MHV), influenza. Herpes Simplex Virus (HSV), Human Immunodeficiency Virus (HIV), MERS etc. MHV receptors function as calcium-dependent adhesion molecule and hence require calcium for utilization by MHV. Further, the calcium channels and pumps are activated in a flexible and precise manner to generate specific calcium signaling, satisfying various spatiotemporal requirements. During the viral infection, host cells modulate calcium-signaling components. On the other hand, viruses utilize host cell components to create a cellular environment that benefits viral lifecycle. Accordingly, targeting the calcium channels may be effective approach to combat SARS-CoV-2 infection.

As on date, there are no effective formulations, drugs or treatment approach against COVID-19. However, there are global initiatives to overcome the pandemic and WHO has executed a Research and Development (R&D) blueprint, which is a global strategy and preparedness plan that allows the rapid activation of R&D activities during pandemics. The objective of blueprint is to fast-track the availability of effective diagnostic tests, vaccines and medicines that are accessible and avert large scale crisis globally.

Calcium channel blockers interrupt the movement of the calcium in cardiac and smooth muscle cells by blocking voltage-gated calcium channels. Calcium channel blockers are widely used in the treatment of hypertension, angina pectoris, supraventricular arrhythmias etc. and recent studies indicate the efficacy of calcium channel blockers against various viruses such as bunya viruses, arenaviruses and flaviviruses.

The mode of administration of drug using a suitable formulation plays an important role in the efficacy of the drug. If the suitable mode is not selected, most of the active ingredient shall be lost in the blood stream while reaching the site of action and may also require the higher dose. As SARS-CoV-2 is associated with pulmonary infection, the formulation shall be effective if directly targeted into lungs.

Pulmonary administration is generally achieved through inhalers or nebulizers or any similar devices. The local therapy with pulmonary administration requires lower dose of the drug thus reducing the probability of occurrence of adverse effects in patients. Pulmonary delivery is an attractive route for systemic administration due to rapid absorption by the larger surface area of the alveolar region, the vasculature and thin air-blood barrier and the avoidance of first pass metabolism.

The inhalers include meter dose inhalers or dry powder inhalers. The meter dose inhalers deliver a specific amount of medication to the lungs in the form of a short burst of aerosolized medicines that are usually self-administered by the patient during inhalation. These inhalers deliver a pre-set amount of medicine through the mouth to the airways. The dry powder inhaler delivers medication to the lungs in the form of a dry powder. The dry powder inhaler drug formulations exhibit greater chemical stability than liquid formulations. A nebulizer is a delivery device in which the medication is fed into the nebulizer in the form of a liquid and the machine then turns this into a fine mist that makes it ideal for addressing respiratory disease and illness.

The Patent Application No. US20050245502A1 titled "Treatments for viral infections" discloses a novel composition comprising therapeutically effective amounts of an anticonvulsant component, such as phenytoin, with at least one calcium channel blocker component or metabolites thereof, a quinoline component, quinoline-quinone component or intermediates or derivatives such as chloroquine, in combination with a multivitamin component. In preferred embodiments, the invention further comprises a quercetin component or one of its derivatives. The components combine and interact in a manner to effectively treat viruses by reducing viral activity in infected subjects.

The Publication entitled "*Calcium channel blocker amlodipine besylate is associated with reduced case fatality rate of COVID-19 patients with hypertension*" by Zhang et. al discloses calcium channel blockers (CCBs), a type of anti-hypertension drugs that are widely used in the clinics that significantly inhibit the post-entry replication events of SARS-CoV-2 in vitro. It also discloses that the comparison with two other major types of anti-hypertension drugs, the angiotensin converting enzyme inhibitors (ACEI) and angiotensin II receptor blockers (ARB), showed that only CCBs display significant anti-SARS-CoV-2 efficacy. The combined treatment with chloroquine and CCBs significantly enhanced the anti-SARS-CoV-2 efficacy. The retrospective clinical investigation of COVID-19 patients revealed that the oral administration of CCB amlodipine besylate distinctly reduced the case fatality rate of patients with hypertension.

The Publication entitled "*The SARS Coronavirus 3a protein binds calcium in its cytoplasmic domain*" by Rinki et. al discloses the expression and purification of the cytoplasmic domain of the 3a protein, called Cyto3a, as a recombinant His-tagged protein in *E. coli*. The calcium binding nature was established by performing various staining methods such as ruthenium red and stains-all, 45Ca overlay method was also done to further support the data. The studies clearly indicate a significant change in the conformation of the Cyto3a protein after binding with calcium. The results strongly suggest that the cytoplasmic domain of the 3a protein of SARS-CoV binds calcium in vitro, causing a change in protein conformation.

As the outbreak of COVID-19 grapples the human population, an urgent need to identify the medical strategies to combat the virus is growing. There are numerous studies disclosing the involvement of calcium channels or pumps in the replication of the viruses but lacks the efficacy due to improper or ineffective administration of the drug.

Hence, in order to overcome the disadvantages that exist in the state of the art, there is need for a formulation along with an effective mode of delivery to block the entry and replication of the virus, which is effective against SARS-CoV-2 virus and COVID-19 in human.

SUMMARY OF THE INVENTION

The present invention overcomes the existing drawbacks by providing a formulation of verapamil hydrochloride for effective antiviral treatment against SARS-CoV-2.

The present invention discloses a formulation of calcium channel blocker for treatment of a novel coronavirus Severe Acute Respiratory Syndrome Coronavirus 2 (SARS-CoV-2) induced Coronavirus Disease 2019 (COVID-19). The formulation comprises verapamil hydrochloride at a concentration between 15 mg/mL and 25 mg/mL, sodium chloride at a concentration of 6.25 mg/mL and distilled water at a volume between q.s. to 1 mL. The formulation is administered as a nasal spray through pulmonary route.

The formulation of verapamil hydrochloride exhibited chemical stability at 60° C. for 33 weeks. These accelerated stability conditions are indicative of the room temperature stability of the nasal spray formulation for up to two years. There was no effect of pH on the chemical stability, but in the formulations with acidic pHs, the pH values increased with time. The pH is maintained without the use of any buffer. In addition, suitable preservatives accepted by US-FDA may be used to prevent microbial growth as it is a multiple dose formulation.

The formulation is analyzed for antiviral activity in-vitro cell lines. The antiviral activity of different concentrations of verapamil hydrochloride is analyzed in human liver cell line, which is grown in Dulbecco's Modified Eagle's Medium (DMEM) supplemented with 5% heat-inactivated fetal bovine serum. The antiviral activity is analyzed against novel SARS-COV-2 (USA-WA1/2020) isolated from an oropharyngeal swab from a patient in Washington. USA (BEI NR-52281). The isolated virus strain is amplified once in Vero E6 cells and had titers of 5×106 plaque-forming units (PFU)/mL. The parameters such as entry, replication of the virus is analyzed and the results indicated that verapamil hydrochloride is effective in inhibition of replication of SARS-CoV-2 through its action on calcium channels on the cell membrane and intracellular storage on endoplasmic reticulum.

Verapamil hydrochloride at a concentration of 10 mg/kg exhibited anti-inflammatory activity in lipopolysaccharide-induced pathological damage in mice. The anti-inflammatory activity of verapamil hydrochloride is attributed to inhibition of the levels of Interleukin-1b (IL-1b), Tumor Necrosis Factor (TNF-a) and Monocyte Chemoattractant Protein-1 (MCP-1) in serum. Verapamil hydrochloride at a concentration of 10 mg/kg exhibited antioxidant activity in lipopolysaccharide-induced pathological damage in mice. The antioxidant activity is due to inhibition of activities of Myeloperoxidase (MPO). Lactate Dehydrogenase (LDH) and Superoxide Dismutase (SOD), Malondialdehyde (MDA) content and lung wet/dry ratio in mouse.

Verapamil hydrochloride is investigated for antiviral activity in patients with Chronic obstructive pulmonary disease (COPD). Verapamil hydrochloride is administered as a nasal spray and saline as a placebo. The results indicated that verapamil hydrochloride increased oxygen saturation from 91.2±12.15 to 95.75±14.57 in patients after inhalation. Verapamil hydrochloride also improved correction of blood pH, blood oxygen pressure and oxygen ratio by maintaining high concentration in alveolar space and dilating the pulmonary vasculature selectivity. This indicates that verapamil hydrochloride is safe and does not produce any adverse effects in patients with COPD.

The formulation of the present invention is administered through pulmonary delivery as a nasal spray using a spray device. The spray device has an ability to deliver a volume of 50 µl to 140 µl in the form of a spray. The droplet size is smaller than 10 µm and the visual plume will be through the manual actuation. The pulmonary administration is simple and effective with lower dose requirement of verapamil hydrochloride with improved tolerance, and patient compliance in addition to effective viral eradication.

BRIEF DESCRIPTION OF THE INVENTION

FIG. 1 illustrates the formulations of verapamil hydrochloride according to an embodiment of the invention.

FIG. 2 illustrates the results of the stability studies of formulations of verapamil hydrochloride at 60° C. for up to 33 days.

DETAILED DESCRIPTION OF THE INVENTION

Figure 3A:
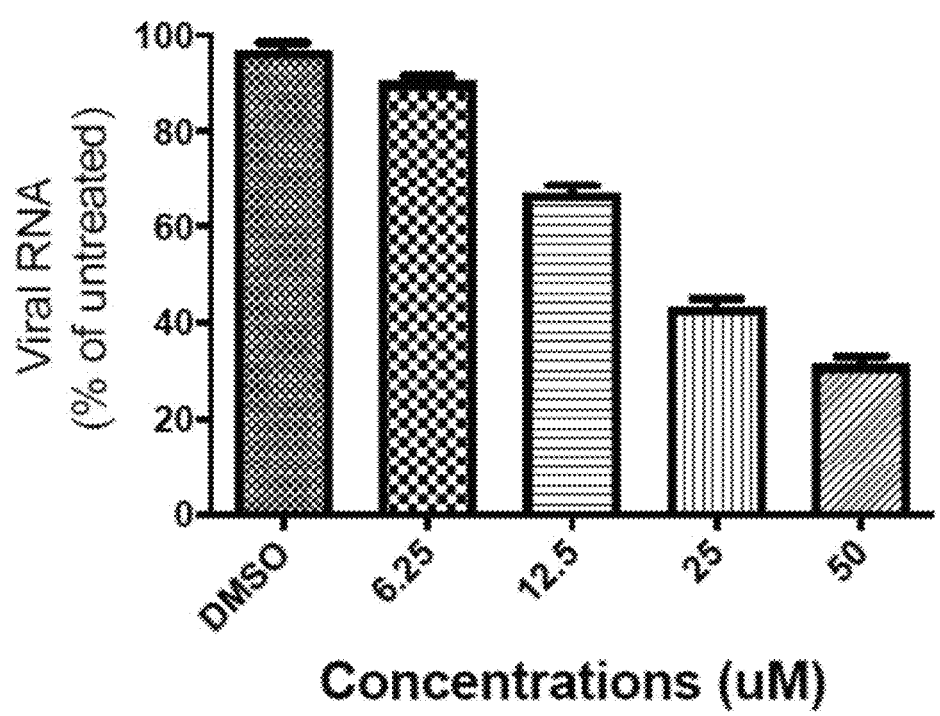
FIG. 3a illustrates the in-vitro antiviral activity of verapamil hydrochloride in SARS-COV-2 infected Huh-7 cell line.

In order to more clearly and concisely describe and point out the subject matter of the claimed invention, the following definitions are provided for specific terms, which are used in the following written description.

The term "Replication" refers to a process in which a cell duplicates into one or more molecules of DNA.

The term "Pulmonary Administration or Inhalation" refers to direct administration of medication into lungs using inhalers, nebulizers or other suitable devices.

The invention relates to a formulation of a calcium channel blocker for nasal delivery. The invention relates to a formulation of verapamil hydrochloride administered through nasal delivery for treatment of a novel coronavirus Severe Acute Respiratory Syndrome Coronavirus 2-induced COVID-19.

Calcium channel blockers are effective in interrupting the calcium pumps or calcium channel by blocking the movement of calcium ions in the cells. The invention discloses a specific drug delivery system comprising a calcium channel blocker for pulmonary delivery.

Generally, calcium channel blockers are broadly classified into dihydropyridine and non-dihydropyridines. According to an embodiment of the invention, different types of calcium channels such as N-Type, L-type and T-type voltage dependent calcium channels may be potential targets to fight against COVID-19.

According to another embodiment of the invention, calcium channel blockers are screened for inhibition of calcium channels to identify the effective calcium channel blocker. The dihydropyridines such as amlodipine, aranidipine, azelnidipine, barnidipine, benidipine, cilnidipine, clevidipine, efonidipine, isadipine, lacidipine, lercanidipine, manidipine, nicardipine, nifedipine, nilvadipine, nimodipine, nisoldipine, nitrendipine, pranidipine are screened for the range of inhibition of various types of calcium channel blockers.

The screening of dihydropyridines is aimed to standardize the dosage required to block the calcium channels effectively in addition to identifying the effective calcium channel blocker. Dihydropyridines are used in a range between 10 mcg to 200 mg per dose and to be analyzed based on the severity of the infection.

The non-dihydropyridine class of calcium channel blockers such as phenylalkylamine including fendiline, gallopamil, verapamil are screened for antiviral activity through calcium channel inhibition. In addition, the class of benzodiazepines, preferably diltiazem, is also screened for antiviral activity against SARS-CoV-2 virus. The non-dihydropyridine and benzodiazepines are used in the range between 10 mcg to 200 mg per dose.

FIG. 1 illustrates the formulations of verapamil hydrochloride according to an embodiment of the invention. The formulation of the present invention comprises verapamil hydrochloride at a concentration between 15 mg/mL to 25 mg/mL, sodium chloride at a concentration of 6.25 mg/mL and distilled water at a volume between q.s. to 1 mL. The formulation is recommended for pulmonary delivery through nasal spray.

According to an embodiment of an invention, the formulation is prepared with different concentrations of verapamil hydrochloride to analyze the stability at an optimum period of time. The formulations with varied concentration of verapamil hydrochloride is prepared in which the formulation 1 comprises verapamil hydrochloride at a concentration of 19.9 mg/mL at pH 5.13, the formulation 2 comprises verapamil hydrochloride at a concentration of 19.9 mg/mL at pH 6.09, the formulation 3 comprises verapamil hydrochloride at a concentration of 19.8 mg/mL at pH 4.63, the formulation 4 comprises verapamil hydrochloride at a concentration of 19.2 mg/mL at pH 5.61 and the formulation 5 comprises verapamil hydrochloride at a concentration of 20.0 mg/mL at 4.09.

FIG. 2 illustrates the results of the stability studies of formulations of verapamil hydrochloride at 60° C. The stability of the formulation comprising various concentration of verapamil hydrochloride is studied at different time intervals at 0 days, 6, 14, 24 days and 33 days to analyze the stability of the formulation. The formulations are stored in 20-mL injection vials at 60° C. The results indicated that formulation did not result in any discoloration after 6 days at 60° C. in any of the samples. However, there was change in pH due to acidic region. The two extra peaks at 2.95 min and 4.25 min are also observed in the standard. Further, no discoloration is observed in any of the samples after 2 weeks at 60° C. The pH values also did not change from 1-week. In addition, no new drug degradation products are observed in any of the five samples suggesting good stability of the formulation.

The stability studies indicate that the formulations are stable at 60° C. for 33 days, which in turn translate to a stability of around 2 years at 25° C. Further, there was no effect of pH on the chemical stability.

According to another embodiment of the invention, verapamil hydrochloride is analyzed for in vitro antiviral activity in SARS-COV-2 infected cell line.

FIG. 3 illustrates the in vitro antiviral activity of verapamil hydrochloride in SARS-COV-2 infected cell line. The antiviral activity of different concentrations of verapamil hydrochloride is analyzed in human liver cell line. Human liver cells are grown in Dulbecco's Modified Eagle's Medium (DMEM) supplemented with 5% heat-inactivated fetal bovine serum. Viral RNA levels are analyzed by quantitative reverse transcription-polymerase chain reaction (qRT-PCR). RNA from cell culture supernatant is extracted using a Viral RNA Mini Kit and qRT-PCR is used to measure viral RNA levels using previously published primers and probes specific for the SARS-COV-2 namely 5'CCGCTGCCCAACACAAG-3' as forward primer, 5'-CCACTAACGTTCTTTTGCAGACAT-3' as reverse primer with 5'-/56-FAM/AGCCTACCT/ZEN/TGACAAGCAATCAGACACTCAA/3IABkFQ-3' as a probe targeting the SARS-COV-2 N1. Viral RNA copies are determined after comparison with a standard curve produced using serial 10-fold dilutions of SARS-COV-2 RNA.

The cytotoxicity of verapamil hydrochloride in Huh7 cells infected with SARS-COV-2 is measured using trypan blue method and percentage cell numbers are quantified using trypan blue after 48 hours. SARS-COV-2 is isolated from oropharyngeal swab from a patient in Washington, USA and after isolation virus strain is amplified in Vero E6 cells to obtain titers of 5×106 plaque-forming units (PFU)/mL. Huh7 cells are pretreated with verapamil hydrochloride at different concentrations of 6.25, 12.5, 25, and 50 uM. Further. Huh7 cells are infected with SARS-CoV-2 at a multiplicity of infection (MOI) of 0.1 for 1 hour, followed by the addition of increasing concentrations of verapamil hydrochloride at a different concentration of 6.25, 12.5, 25, and 50 uM and 0.1% DMSO is used as control. The cell culture supernatants are collected at 48 hours after infection and viral RNA copies are measured by RT-PCR.

Figure 3B:
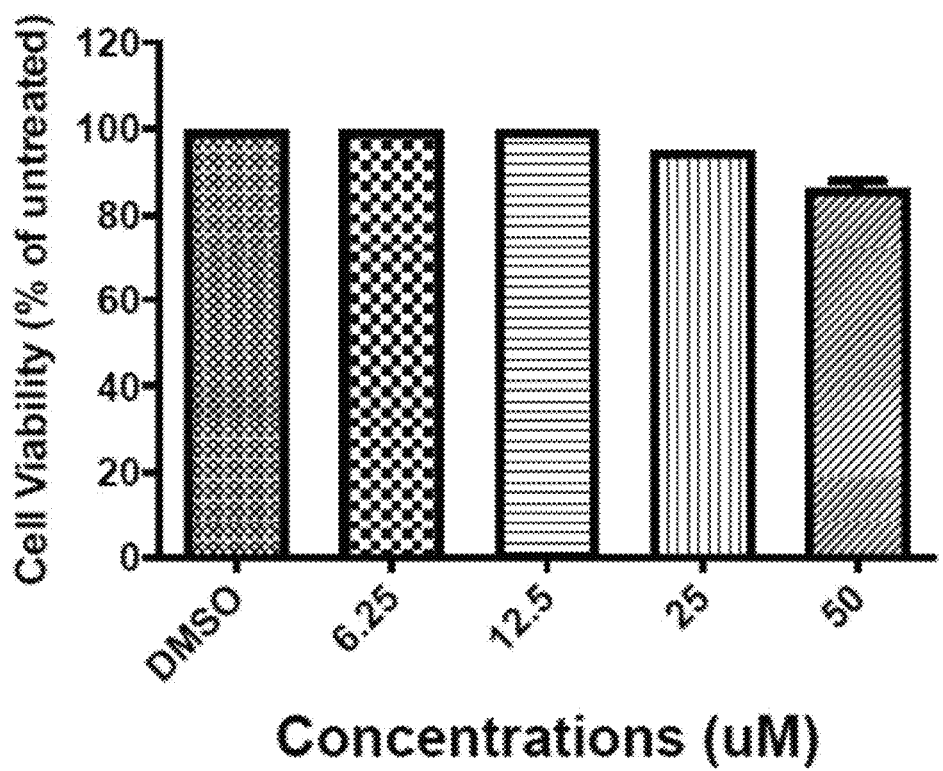
FIG. 3b illustrates reduction in cell viability in SARS-COV-2 infected Huh-7 cell line.

FIG. 3a illustrates the in vitro antiviral activity of verapamil hydrochloride in SARS-COV-2 infected cell line and FIG. 3b illustrates reduction in cell viability in SARS-COV-2 infected cell line treated with verapamil hydrochloride. The results indicated that the treatment of cells with verapamil hydrochloride resulted in a dose-dependent reduction in the viral RNA in the supernatant compared to the DMSO at 48 hours after infection. Verapamil hydrochloride showed no significant toxicity against Huh7 cells at the used concentration at 48 hours. This interprets the in-vitro antiviral activity of verapamil hydrochloride.

The in-vitro cell-based assay is performed using the CaCo-2 cell lines using DMSO as a solvent and suitable growth medium. Verapamil hydrochloride is used at a concentration in the range between 0.032 µg/ml to 100 µg/ml. The assay includes M 128533 as a positive control. The EC90 (compound concentration that reduces viral replication by 90%) for the positive control is estimated to be 11 µg/ml and for hydrochloride is found to be 6.9 µg/ml in inhibiting the 90% of the viral replication in the experimental conditions. This experiment indicates potent anti-viral (SARS-COV2) effect of verapamil hydrochloride through its unique calcium channel blocking mechanism.

Verapamil hydrochloride exerts antiviral activity through modulation of an entry, replication and release of SARS-COV2 through its action on calcium channels on the cell membrane as well as intracellular storage on endoplasmic reticulum. Verapamil hydrochloride targets the calcium channel and inhibits the movement of calcium thus halting the calcium signaling in the cell systems. Calcium plays an important role in the adherence, replication and multiplication in the host cell. Once the virus enters the host cell, it utilizes the components of the host cell for replication and results in disruption of the host cell mechanisms including the calcium homeostasis thus altering the signal transduction in the host cell for survival and multiplication of the virus.

The various host cell calcium channels and pumps including different voltage gated calcium channels, store operated channels, receptor operated channels, transient receptor potential ion channels and Calcium-ATPase etc. mediate the mobilization of secondary metabolite calcium across the plasma membranes and subcellular organelles thus modulating the intracellular free calcium. The intracellular calcium and the calcium channels play an important role in the viral-host interaction and viral pathogenesis in the host cell. These calcium channels and pumps are disrupted due to viral invasion leading to imbalance of intracellular calcium. As a result of which the viral growth is enhanced affecting the host cell morbidity.

The effect of verapamil hydrochloride is analyzed in lipopolysaccharide-induced pathological damage in mouse. In order to analyze the effect of verapamil hydrochloride on inflammation and oxidative stress, the levels of Interleukin-1b (IL-1b). Tumor Necrosis Factor (TNF-a) and Monocyte Chemoattractant Protein-1 (MCP-1) in serum and activities of Myeloperoxidase (MPO), Lactate Dehydrogenase (LDH) and Superoxide Dismutase (SOD), Malondialdehyde (MDA) content and lung wet/dry ratio.

Figure 4:
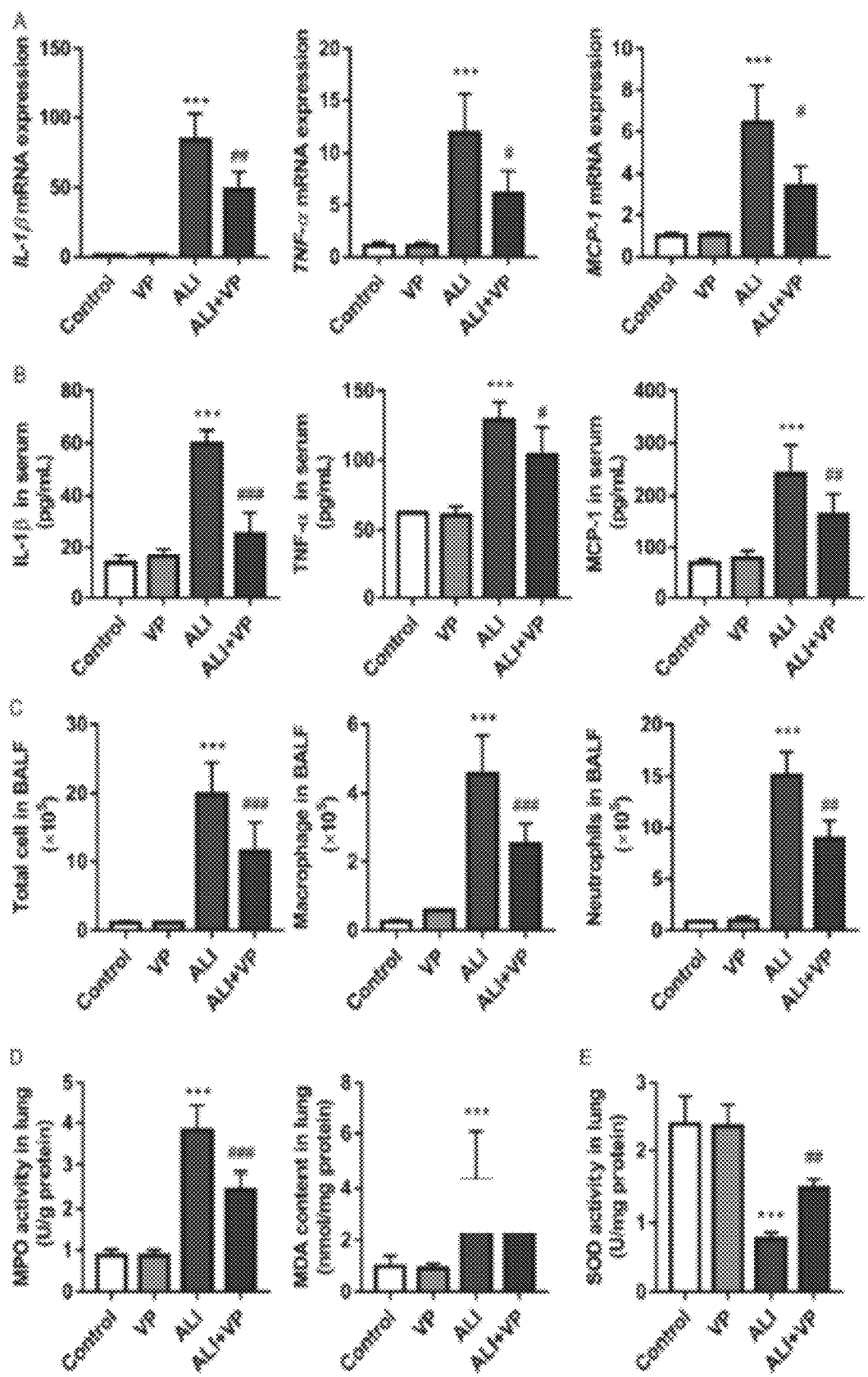
FIG. 4 illustrates the effect of verapamil hydrochloride against lipopolysaccharide-induced pathological damage in mice.

FIG. 4 illustrates the effect of verapamil hydrochloride against lipopolysaccharide-induced pathological damage in mice. Mice are treated with 5 mg/kg of lipopolysaccharide. Two hours later, mice are treated with verapamil hydrochloride at a concentration of 10 mg/kg and saline as control and observed for 10 hours. The levels of IN-1b, TNF-a, MCP-1 in serum is analyzed using ELISA and activities of MPO, LDH, SOD and MDA is analyzed in addition to lung wet/dry ratio. The effect of verapamil hydrochloride on total cells, macrophages and neutrophils in Bronchoalveolar Lavage Fluid (BALF) is also analyzed.

The results indicated that verapamil hydrochloride exhibited anti-inflammatory activity by reducing the serum levels of IN-1b, TNF-a, MCP-1 and total cells, macrophages and neutrophils in BALF. In addition, the activities of MPO. LDH, SOD and MDA levels are reduced in lung tissue in response to verapamil hydrochloride. This indicates the anti-inflammatory and antioxidant activity of verapamil hydrochloride in mice.

Verapamil hydrochloride is analyzed for antiviral activity in patients with Chronic obstructive pulmonary disease (COPD). A double-blind placebo trial is conducted to analyze the effect of verapamil hydrochloride in patients admitted in Intensive Care Unit (ICU). Verapamil hydrochloride is administered as a nasal spray and saline as a placebo. The results indicated that verapamil hydrochloride increased oxygen saturation from 91.2±12.15 to 95.75±14.57 in patients after inhalation. Verapamil hydrochloride also improved correction of blood pH, blood oxygen pressure and oxygen ratio by maintaining high concentration in alveolar space and dilating the pulmonary vasculature selectivity. This indicates that verapamil hydrochloride is safe and does not induce any adverse effects in patients with COPD.

According to another embodiment of the invention, verapamil hydrochloride is administered through pulmonary administration or inhalation using a nasal spray. The efficacy of a drug varies with the mode of administration and the drug may require more time to reach the site of action or may alter its efficacy while in the blood stream. The pharmacokinetics and the pharmacodynamics of the drug plays an important role in determining the efficacy of the drug. Hence, the mode of administration is very critical. Calcium channel blockers are administered through pulmonary route, which directly targets the lung where the severity of the infection is high.

SARS-COV2 viral infection results in the respiratory illness, breathing complications and pneumonia like symptoms affecting the lungs of a patient. Hence, direct pulmonary administration has an advantage for effective drug delivery without passing through the blood stream for a long time and decreasing the dosage due to direct administration.

The pulmonary administration or inhalation of calcium channel blockers is achieved using unique drug delivery systems such as inhalers or nebulizers. In addition to nasal spray, the invention can also expand to different types of inhalers such as pressurized metered dose inhalers, dry powder inhalers, multi-dose liquid inhalers and soft-mist inhalers for pulmonary administration. Similarly, small-volume nebulizer (SVN), breath-actuated jet nebulizer, vibrating mesh nebulizer, jet nebulizer with virtual valve technology, perforated oscillating membrane device, and deep tube oral spray device are effective in delivering the calcium channel blockers as monotherapy or in combination for the treatment of COVID-19.

The inhalers and nebulizers are simple and effective in pulmonary administration with lower dose requirement of drug. The pulmonary administration results in delivering precise and consistent doses to a targeted region in the lungs and maintain the stability of the delivered drugs.

Even though the calcium channel blockers are effective in inhibiting the mobility of intracellular calcium by disrupting the calcium channel blockers, the antiviral activity against SARS-CoV-2 varies with the type of calcium channel blocker.

The pulmonary administration of the calcium channel blockers or antagonists requires only low dose of the drug due to its local pharmacological action in lungs compared to oral or any other route of administration. The pulmonary administration is also associated with improved tolerance, patient compliance and also with effective viral eradication.

The formulation of verapamil hydrochloride is administered as a nasal spray with a concentration in the range between 15 mg/mL to 20 mg/mL. However, in addition the nasal spray bottle actuator has the ability to deliver less concentration of the drug i.e., 2.5 mg/actuation or spray. The nasal spray has the ability to deliver up to 140 ul of the solution and the concentration administered is 2.5 mg/125 ul.

The nasal spray of the formulation of the present invention is administrated through a spray device. The spray device has the capability of administering dose volume in the range between 50 µl to 140 µl of the formulation with a droplet size less than 10 µm as tested by laser diffraction method.

The nasal spray of verapamil hydrochloride reduces the dose requirement as targeted delivery in nose which allows the entry of the virus and passage through upper respiratory and then lower respiratory tract. The nasal spray is also associated with ease of administration, improved patient compliance, self-administration without requirement of health professional and is also cost-effective.

The formulation of the invention may be useful as add-on therapy to the recommended standard of care for the patients who are moderately severe thus improving the disease outcome in patients. The treatment may be administered to patients who have tested positive for SARS-COV-2 virus at an early stage as well as those who have serious pneumonia like complications leading to Acute Respiratory Distress Syndrome (ARDS).

What is claimed is:

1. A method for treating SARS-CoV-2 induced COVID-19 in a person who has tested positive for SARS-CoV-2 induced COVID-19, the method comprising administering to the person a pharmaceutically acceptable composition containing a calcium channel blocker component via nasal administration, the calcium channel blocker component comprising an amount of verapamil that is effective to treat the SARS-CoV-2 induced COVID-19, wherein a) the concentration of verapamil in the composition is 15-25 mg/mL, b) the composition is maintained at a pH between 4.09 and 6.09 prior to administration, and c) the composition is administered through a nasal spray device.

2. The method of claim 1, wherein each actuation of the nasal spray device delivers a volume of 50 µl to 140 µl of the composition.

* * * * *